United States Patent [19]

Taschner

[11] Patent Number: 4,820,499

[45] Date of Patent: Apr. 11, 1989

[54] CLOSURE FOR A STERILIZING CONTAINER

[75] Inventor: Wolfgang Taschner, Tuttlingen, Fed. Rep. of Germany

[73] Assignee: Aesculap-Werke AG, Fed. Rep. of Germany

[21] Appl. No.: 931,180

[22] Filed: Nov. 14, 1986

[30] Foreign Application Priority Data

Nov. 22, 1985 [DE]  Fed. Rep. of Germany ....... 3541309

[51] Int. Cl.$^4$ .................. A61L 2/00; B65D 45/16; B65D 55/02
[52] U.S. Cl. ...................................... 422/310; 422/26; 422/119; 422/300; 436/1; 220/214; 220/324; 206/438; 206/459; 206/807
[58] Field of Search .............. 422/26, 119, 300, 310; 436/1; 220/214, 324, 78; 206/438, 459, 807

[56] References Cited

U.S. PATENT DOCUMENTS

| | | | |
|---|---|---|---|
| 4,023,678 | 5/1977 | Fiedler | 206/459 X |
| 4,562,047 | 12/1985 | Sestak et al. | 422/119 X |
| 4,570,818 | 2/1986 | Borst et al. | 206/459 X |
| 4,609,125 | 9/1986 | Willingham | 220/324 |
| 4,625,885 | 12/1986 | Nichols | 422/119 X |

FOREIGN PATENT DOCUMENTS 3116036  11/1982  Fed. Rep. of Germany ...... 422/310

Primary Examiner—Barry S. Richman
Assistant Examiner—Lynn M. Kummert
Attorney, Agent, or Firm—Wolf, Greenfield & Sacks

[57] ABSTRACT

To eliminate the necessity for additional seals or indicator tapes in a closure for a sterilizing container comprising a bottom part and a lid, with a pivotable locking bar which in a closed position fixes the lid in the closed position on the bottom part and in an open position releases the lid for removal from the bottom part, and with a safety closure for the locking bar which is damaged when the locking bar is pivoted from the closed position to the open position, the safety closure includes (i) a data carrier card which can be pushed into or put into a holding device on the locking bar, on the lid, or on the bottom part, (ii) a securing member to prevent removal of the data carrier card from the holding device when the locking bar is in the closed state, and (iii) a marking element to penetrate the data carrier card secured in the holding device during pivotal motion of the locking bar from the closed position to the open position.

7 Claims, 2 Drawing Sheets

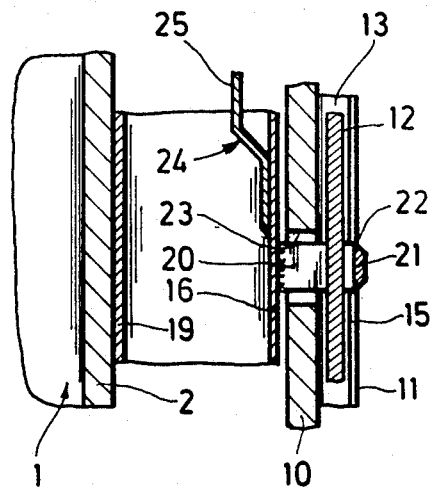
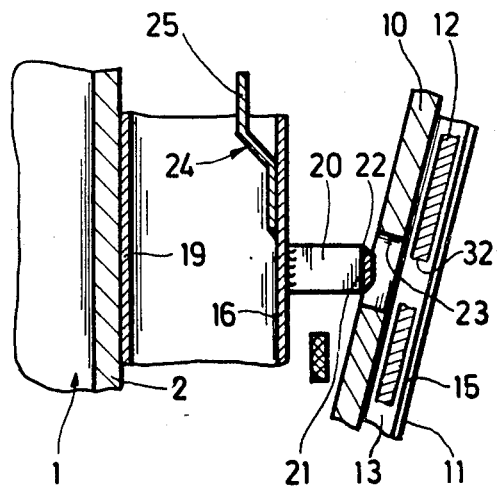
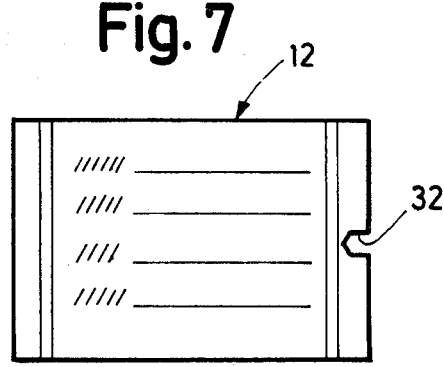

CLOSURE FOR A STERILIZING CONTAINER

The invention relates to a closure for a sterilizing container comprising a bottom part and a lid, with a pivotable locking bar which in a closed position fixes the lid in the closed position on the bottom part and in an open position releases the lid for removal from the bottom part, and with an opening safety means for the locking bar which is damaged when the locking bar is pivoted from the closed position to the open position.

After the sterilization procedure, sterilizing containers for medical instruments must be kept closed until use in order to maintain the sterile state of the contents. On the one hand, to prevent unintentional opening prior to actual use, and, on the other hand, to ensure that unintentional opening prior to use can be detected, closures for sterilizing containers are often provided with seals which must be destroyed to enable opening of the locking bar. It is also known to use so-called indicator adhesive tapes as seals, i.e., tapes which change their color during sterilization. The locking bar of such a sterilizing container can only be opened by destroying such an indicator adhesive tape (German Patent No. 3 116 036).

All known devices require additional elements to safeguard the closed state, such as, for example, wire or plastic seals or indicator adhesive tapes.

The object of the invention is to further develop a closure of the generic kind so as to eliminate the necessity for any additional sealing means for ensuring continuous closure of a sterilizing container until use.

This object is achieved in accordance with the invention in a closure of the kind described at the outset by the opening safety means being constituted by a data carrier card which, can be pushed into or put into a holding device on the locking bar, on the lid, or on the bottom part, by a securing member preventing removal of the data carrier card from the holding device when the locking bar is in the closed state, and by a marking element penetrating the data carrier card secured in the holding device during pivotal motion of the locking bar from the closed position to the open position.

Such data carrier cards are used regularly in special holding devices on sterilizing containers to provide information on the contents of the sterilizing container and, in appropriate instances, on prior treatment. For example, the sterilizing date, the expiration date, the batch number and the name of the person responsible for the sterilization are entered on such data carrier cards. These data carrier cards are exchangeably arranged in an appropriate holding device on the sterilizing container and may, for example, be in the form of small cardboard cards which are insertable into the holding device.

In accordance with the invention, it is proposed that these data carrier cards which are provided on every sterilizing container anyhow be simultaneously used to ensure continuous closure. To this end, the holding devices with the data carrier cards are so arranged on the locking bar itself or on the container that the opening motion of the locking bar causes a marking element to penetrate and damage the data carrier card so that it is evident from the data carrier card that the locking bar has been opened. To also ensure that the data carrier card cannot be exchanged unintentionally, a securing member is provided to close the holding device when the locking bar is closed, so that the data carrier card can only be removed from the holding device when the locking bar is in the open state.

In this way, a double effect is obtained, namely, on the one hand, the data carrier card is secured against unintentional removal so long as the sterilizing container is closed, and, on the other hand, this data carrier card which is necessary anyway is used as an indicator of whether the sterilizing container has been opened unintentionally. All in all, a substantially simplified design of such a sterilizing container is attained since additional sealing means are no longer required.

In a preferred embodiment, the marking element is in the form of a puncher which punches a hole or a notch in the data carrier card as it penetrates it. This results in defined, easily visible damage to the data carrier card which immediately indicates that the sterilizing container has been opened prior to use.

The marking element may be in the form of a simple pin which sinks into the data carrier card as the locking bar opens. This embodiment does, however, have the disadvantage that the marking element sinking into the data carrier card in the opening position of the locking bar impedes removal of the data carrier card when the locking bar is in the opened state. For this reason, it is advantageous for the marking element to project laterally into the area of the data carrier card and to be so arranged that it penetrates the data carrier card between open position and closed position, but releases it in the open position and in the closed position. The marking element, therefore, only comes into contact with the data carrier during the actual pivotal motion of the locking bar, more particularly, during both pivoting from the open position to the closed position and pivoting from the closed position to the open position. This, furthermore, ensures that a data carrier card is not inserted into the holding device until the sterilizing container has been closed since in the event of introduction prior to closure of the locking bar, the data carrier card would also be damaged by the marking element during the closing motion of the locking bar. If a container in use exhibits an undamaged data carrier card, this is proof that the locking bar was closed when the data carrier card was inserted and that the locking bar remained in this closed position until use. It also indicates that the data carrier card is the original data carrier card since the securing member makes removal of the data carrier card impossible when the locking bar is in the closed state.

The securing member preferably releases the holding device when the locking bar is in the open state so as to enable simple removal of the data carrier card from the holding device after intentional opening of the container. In a preferred embodiment, the securing member closes an insertion slot for the data carrier card, when the locking bar is in the closed state, and it is elastically so displaceable that the data carrier card on insertion displaces the securing member elastically out of the position closing the insertion slot, whereas it remains in the position closing the insertion slot when the data carrier card is pushed out of the holding device. The securing member, therefore, enables the data carrier card to be inserted at any time into the holding device, but secures the card in the holding device after insertion so long as the locking bar remains closed. This is a one-way safety means which may be constructed in various ways, for example, using pivotable prongs which as in the case of a mailbox slot fall under their own weight into a closed position and can be pushed aside by the inserted card.

In a particularly advantageous embodiment, the securing member includes one or several leaf springs which cover the insertion slot transversely and comprise at their free ends, ends which are bent into the interior of the holding device and rest against a wall of the holding device which delimits the insertion slot. While the data carrier card is being pushed in, it is directed by the bent free ends of the leaf springs into close abutment with the delimiting wall and on further insertion presses the leaf springs slightly to the side, but, on the other hand, when an attempt is made to pull the data carrier card out of the holding device, it rests against the underside of the leaf springs on account of the bent free ends and is prevented from being pulled out of the holding device.

In principle, it is possible for the holding device to be arranged with the data carrier card on the bottom part or on the lid, in which case, the marking element and the securing member are carried by the locking bar. An embodiment is, however, preferred wherein the holding device is arranged on the outer side of the locking bar, and wherein the marking element held on the bottom part and also the securing member likewise held on the bottom part extend through openings in the locking bar. In this embodiment, the holding device is located on the outer side of the locking bar and is, therefore, freely accessible and clearly visible so that the data carrier card inserted into the holding device is easy to read.

The following description of a preferred embodiment serves in conjunction with the appended drawings to explain the invention in greater detail.

FIG. 5 is an enlarged detailed view of section A in FIG. 3;

FIG. 6 is an enlarged detailed view of section B in FIG. 4; and

FIG. 7 is a plan view of a data carrier card marked with a notch.

Figure 1:
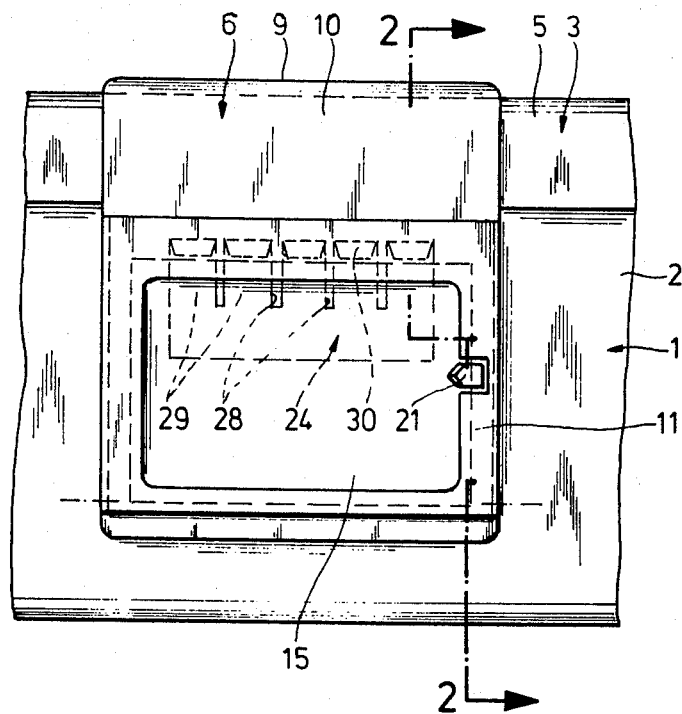
FIG. 1 is a plan view of the locking bar of a sterilizing container.

The sterilizing container includes a tub-shaped bottom part 1 with side walls 2 and a lid 3 set onto it. The lid rests sealed by an annular seal 4 on the upper edge of the side walls 2 and overlaps this bearing point with an edge 5 drawn downwardly in flange-type configuration. Arranged on opposite sides of the sterilizing container to fix the lid 3 on the bottom part 1 are locking bar closure means. The drawings illustrate the closure on one side only.

Figure 4:
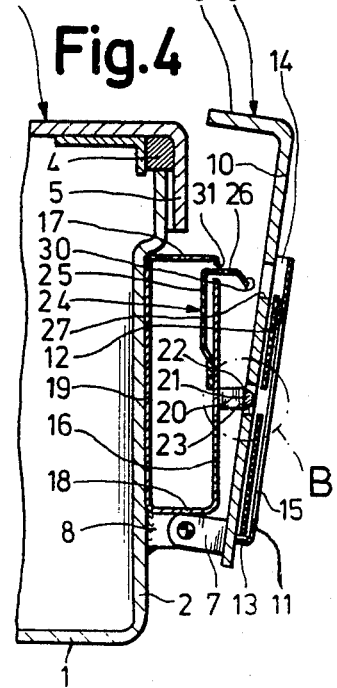
FIG. 4 is a view similar to FIG. 3 with the locking bar in the open state.

This locking bar closure means includes an L-shaped locking bar 6 which is mounted at one of its ends, via arms 7 protruding perpendicularly from it, at corresponding arms 8 protruding from the side wall of the bottom part, for pivotal motion about a horizontal axis of rotation extending parallel to the side wall. This locking bar 6 can be pivoted between a closed position in which its shorter leg 9 overlaps the cover 3 (FIG. 2) and an open position in which the leg 9 releases the lid 3 for removal from the bottom part (FIG. 4). Stops and detent means, not illustrated in the drawings, may be provided to fix the locking bar in the closed position and release it only after special actuation of these detent means. Stops which define the open position may also be provided so that in the open position the locking bar cannot be fully tilted away from the container.

The locking bar carries on the outer side of its long leg 10 a frame 11 extending parallel to this leg and arranged in spaced relation thereof. Together with the leg 10, the frame forms a holding device for a data carrier card 12 made, for example, of cardboard. To this end, the frame 11 is joined to the leg 10 via lateral webs 13 extending along the side edges and the lower edge of the frame 11. On the upper edge of the frame 11, there are no such webs so that the insertion slot 14 there between leg 10 and frame 11 remains free for the data carrier card 12. The frame 11 encloses a display window 15 through which a data carrier card 12 inserted into the holding device can be read.

Arranged on the side wall 2 of the bottom part 1, in the area covered by the locking bar 6, is a supporting wall 16 extending parallel to the side wall and in spaced relation thereto, which is connected via cross members 17 and 18 to an attachment wall 19 extending parallel to the supporting wall 16. The attachment wall 19 rests against the side wall 2 and is firmly connected, for example, welded thereto, in this area.

Attached to the supporting wall 16 is a holder 20 which protrudes perpendicularly outwardly therefrom and carries at its free end a marking element 21 extending parallel to the supporting wall 16. This marking element 21 is constructed as a puncher, i.e., it exhibits sharp edges 22 on its side facing the bottom part 1.

The distance of the marking element 21 from the supporting wall 16 is so selected that when the locking bar is in the closed state, the marking element 21 protrudes through an opening 23 in the locking bar and lies outside of the accommodating area formed by the holding device for the data carrier card 12 (FIG. 5). When the locking bar is in the open state, the marking element 21 is, on the other hand, located on the side of this accommodating area facing the bottom part, i.e., when the locking bar is pivoted from the open position to the closed position, the marking element 21 protrudes through the entire accommodating area formed by the holding device for the data carrier card (FIG. 6).

The holder 20 with the marking element 21 is so positioned that the holder 20 lies at the edge of the accommodating area formed by the frame 11 so that a data carrier card 12 inserted into the accommodating area is not obstructed by the holder, whereas the marking element 21 projects into the space which is occupied by a data carrier card 12 when pushed into the holding device (FIG. 1).

The opening 23 in the locking bar 6 is only of slightly larger construction than holder 20 and marking element 21 so that the edges of the opening 23 and the edges 22 of the marking element 21 slide snugly past one another when the locking bar is pivoted. The edges of the opening 23 thus cooperate with the edges 22 of the marking element 21 so that when the locking bar is pivoted from the closed position to the open position, a notch is punched in a data carrier card located in the holding device. Such a data carrier card with a notch 32 is illustrated in FIG. 7.

Figure 2:
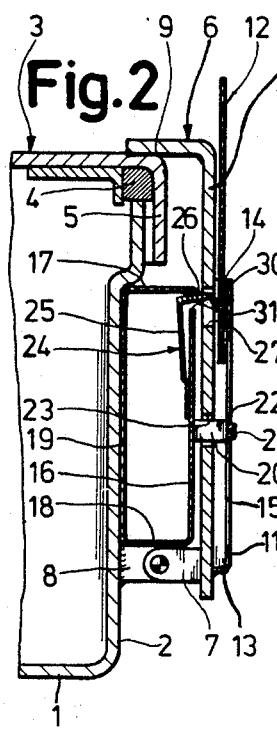
FIG. 2 is a sectional view taken on line 2—2 in FIG. 1, with the locking bar in the closed state during insertion of a data carrier card.
Figure 3:
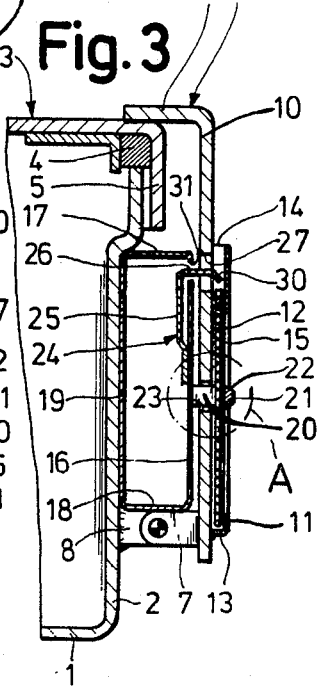
FIG. 3 is a view similar to FIG. 2 with an inserted data carrier card.

A securing member 24 of substantially plate-shaped construction and L-shaped cross-section is attached to the side of the supporting wall 16 facing the bottom part 1. A leg 25 is attached at its free end to the supporting wall 16, while the other leg 26 protrudes through an opening 27 in the supporting wall perpendicularly out of the latter. The leg 26 exhibits a number of parallel incisions 28 so that the leg 26 is divided up into several adjacent webs 29. These webs 29 comprise at their free ends downwardly oriented bent portions 30 which, when the locking bar is in the closed state, protrude through an opening 31 in the locking bar 6 and rest against the inner side of the frame 11 (FIG. 3) so that these webs 29 completely cover the insertion slot 14 when the locking bar 6 is closed. The securing member 24 consists of an elastic material, for example, a spring sheet metal, so that the webs 29 may be elastically moved away from the frame 11 out of their resting position against the inner side of the frame 11. This enables insertion of a data carrier card 12 from above through the insertion slot 14 into the holding device when the locking bar is closed. In this case, the lower edge of the data carrier card slides at the inwardly oriented bent portions 30 against the inner side of the frame 11 and then elastically bends the webs 29 back so that the data carrier card can be pushed past the webs 29 into the holding device (FIG. 2). Once the data carrier card has been fully inserted, the free ends of the webs 29 come to rest again against the inner side of the frame 11 so that the data carrier card is secured against unintentional removal from the holding device (Figure 3). If the data carrier card is pushed upwardly, the upper edge of the data carrier card 12 is pushed against the bent portions 30 from below and thus slides underneath the webs 29 so that the data carrier card is prevented from being pushed further out of the holding device.

In operation, the sterilizing container is closed for the sterilization. The locking bar is then in the closed position illustrated in FIG. 2. A data carrier card is pushed from above into the holding device and is secured against loss therein.

When the locking bar is pivoted into the open position, the marking element 21 passes through the interior of the holding device and in doing so punches a notch 32 in the data carrier card arranged in the holding device. When the locking bar 6 is closed again afterwards, it is readily recognizable from this notch 32 that the locking bar has been opened at least once before. Absence of a data carrier card indicates that a hundred-percent control is not guaranteed and the contents of the sterilizing container are, therefore, not to be used.

When the locking bar is opened according to specification, the data carrier card can be readily pushed out of the holding device after opening, since the securing member 24 releases the data carrier card in the holding device when the locking bar is in the open state (FIG. 4).

This construction also ensures that the data carrier card is not inserted until the locking bar has assumed its closed position. If the data carrier card is inserted into the holding device prior to closure of the locking bar, the data carrier card is likewise damaged by the marking element during closure. Accordingly, an undamaged data carrier card indicates that it has been inserted when the locking bar was in the closed state and that the locking bar has since not been pivoted into the open position.

The construction indicated hereinabove simultaneously offers the advantage that the data carrier card which indicates vital data of the container contents is kept safely on the container, i.e., is prevented from loss so long as the locking bar remains in the closed position.

What is claimed is:

1. Closure for a sterilizing container comprising a bottom part and a lid, with a pivotable locking bar which in a closed position fixes the lid in the closed position on the bottom part and in an open position releases the lid for removal from the bottom part, and with an opening safety means for the locking bar which is damaged when the locking bar is pivoted from the closed position to the open position, wherein the improvement comprises having an opening safety means comprising
   a data carrier card which can be pushed into or put into an interior of a holding device, on the sterilizing container
   a securing member that prevents removal of the data carrier card from the holding device when the locking bar is in the closed position, and
   a marking element that penetrates the data carrier card secured in the holding device during pivotal motion of the locking bar from the closed position to the open position.

2. Closure as defined in claim 1, characterized in that the marking element is in the form of a puncher which punches a hole or a notch in the data carrier card on penetrating it.

3. Closure as defined in claim 1, characterized in that the marking element projects laterally so that a portion of the marking element to lies parallel to the data carier card and is so arranged that it penetrates the data carrier card between open position and closed position, but is clear of it in the open position and in the closed position.

4. Closure as defined in claim 1, characterized in that the securing member releases the holding device when the locking bar is moved to
   the open position.

5. Closure as defined in claim 1, characterized in that the holding device is arranged on the side of the locking bar facing away from said bottom part , and in that the marking element held on the bottom part and also the securing member likewise held on the bottom part protrude through openings in the locking bar 6 .

6. Closure as defined in claim 1, characterized in that when the locking bar is in the closed position, the securing member closes an insertion slot for the data carrier card and is elastically so displaceable that when the data carrier card is pushed in, it displaces the securing member elastically out of the position closing the insertion slot, whereas it remains in the position closing the insertion slot when the data carrier card is removed from the holding device when the locking bar is in the open position.

7. Closure as defined in claim 6, characterized in that the securing member includes one or several webs which transversely cover the insertion slot and comprise at their free ends, ends bent over at the interior of the holding device delimiting the insertion slot.

\* \* \* \* \*